(12) United States Patent
Karni

(10) Patent No.: US 9,545,284 B2
(45) Date of Patent: Jan. 17, 2017

(54) DEVICES AND METHODS FOR DERMATOLOGICAL TREATMENT

(75) Inventor: Ziv Karni, Kfar Shmaryahu (IL)

(73) Assignee: ALMA LASERS LTD., Caesarea (IL)

( * ) Notice: Subject to any disclaimer, the term of this patent is extended or adjusted under 35 U.S.C. 154(b) by 642 days.

(21) Appl. No.: 13/265,883

(22) PCT Filed: Apr. 28, 2010

(86) PCT No.: PCT/IB2010/051864
§ 371 (c)(1),
(2), (4) Date: Oct. 24, 2011

(87) PCT Pub. No.: WO2010/125531
PCT Pub. Date: Nov. 4, 2010

(65) Prior Publication Data
US 2012/0041525 A1     Feb. 16, 2012

Related U.S. Application Data

(60) Provisional application No. 61/174,004, filed on Apr. 30, 2009.

(51) Int. Cl.
| | |
|---|---|
| *A61N 1/32* | (2006.01) |
| *A61N 5/06* | (2006.01) |
| *A61N 7/00* | (2006.01) |
| *A61B 18/02* | (2006.01) |
| *A61B 17/00* | (2006.01) |
| *A61B 18/00* | (2006.01) |

(52) U.S. Cl.
CPC ...... *A61B 18/02* (2013.01); *A61B 2017/00747* (2013.01); *A61B 2018/00095* (2013.01); *A61B 2018/00101* (2013.01); *A61B 2018/0243* (2013.01)

(58) Field of Classification Search
None
See application file for complete search history.

(56) References Cited

U.S. PATENT DOCUMENTS

| | | |
|---|---|---|
| 4,206,609 A | 6/1980 | Durenec |
| 5,596,875 A | 1/1997 | Berry et al. |
| 5,759,182 A | 6/1998 | Varney et al. |
| 6,017,337 A | 1/2000 | Pira |
| 6,096,178 A | 8/2000 | Amirav et al. |

(Continued)

FOREIGN PATENT DOCUMENTS

| | | |
|---|---|---|
| WO | WO 2008/055243 | 5/2008 |
| WO | WO2008/083305 | 7/2008 |

OTHER PUBLICATIONS

PCT Search report of PCT/IB2010/051864 (parent case) mailed Sep. 14, 2010.

(Continued)

*Primary Examiner* — Brian T Gedeon

(57) ABSTRACT

Disclosed are methods for dermatological treatment that in some embodiments include contacting a plurality of cooling probes with an area of skin and maintaining the plurality of cooling probes in contact with the area of skin for a period of time while the distal ends of the plurality of cooling probes substantially cool a volume of tissue, thereby causing a beneficial effect as a result of the substantial cooling of the volume of tissue, as well as devices useful for implementing the method.

24 Claims, 4 Drawing Sheets

(56) References Cited

U.S. PATENT DOCUMENTS

| | | |
|---|---|---|
| 6,430,956 B1 | 8/2002 | Haas et al. |
| 6,503,246 B1 | 1/2003 | Har-Shai et al. |
| 6,629,417 B2 | 10/2003 | Haas et al. |
| 7,850,683 B2 * | 12/2010 | Elkins et al. .................... 606/25 |
| 2007/0129714 A1 * | 6/2007 | Elkins et al. .................... 606/21 |
| 2008/0119839 A1 | 5/2008 | Vancelette |

OTHER PUBLICATIONS

PCT Search opinion of PCT/IB2010/051864 (parent case), mailed Sep. 14, 2010.
PCT Preliminary patentability opinion of PCT/IB2010/051864 (parent case), mailed Sep. 14, 2010.
U.S. Appl. No. 61/087,036, filed Aug. 7 2008. The provisional application is parent to PCT/US2009/053153 and through it to U.S. Appl. No. 13/057,939.

* cited by examiner

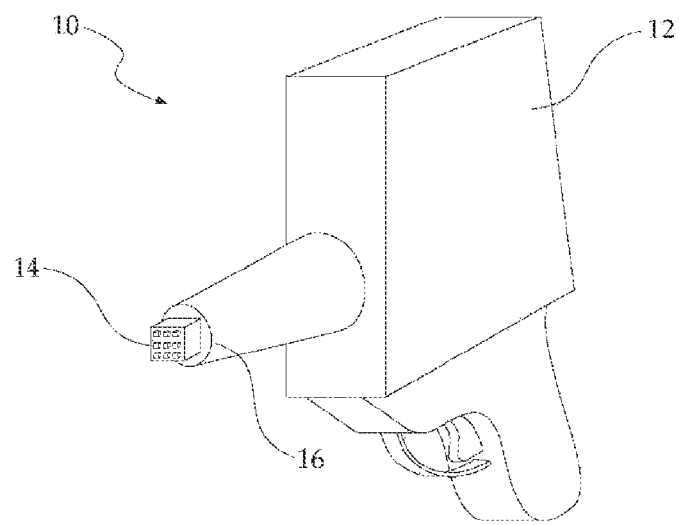
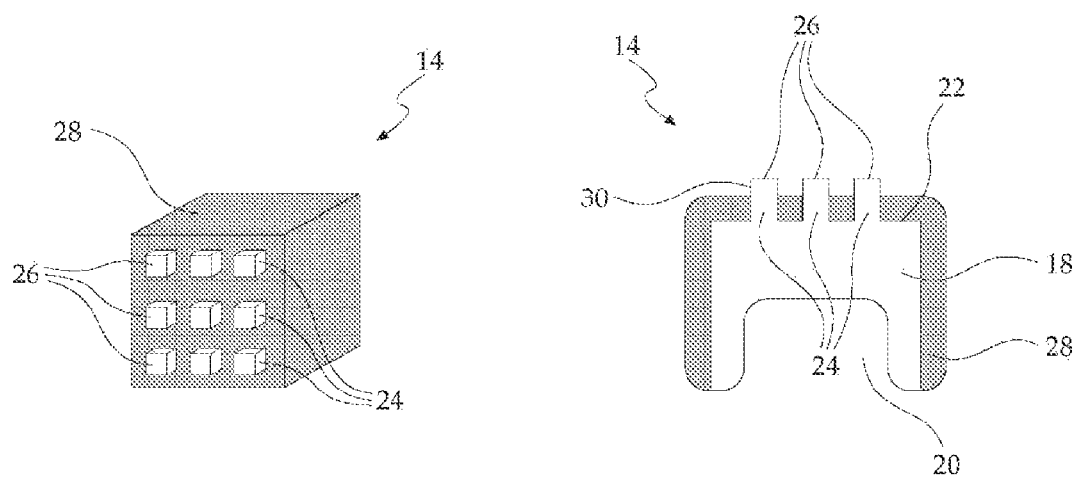
FIG. 1A
FIG. 1B
FIG. 1C

DEVICES AND METHODS FOR DERMATOLOGICAL TREATMENT

This Application is a national phase of, and claims priority from, PCT Application No. PCT/IB2010/051864, filed on Apr. 28, 2010, which claims priority from US Provisional Application No. 61/174,004, filed on Apr. 30, 2009, both of which are hereby incorporated by reference as if fully set forth herein.

FIELD OF THE INVENTION

The invention, in some embodiments, relates to the field of dermatological treatment, and more particularly, but not exclusively, to methods and devices for dermatological treatment.

BACKGROUND OF THE INVENTION

The skin is a complex multi-layered organ. The outer layer of the skin is the epidermis having a thickness of between 0.05 mm (eyelids) and 1.5 mm (palms and soles) made up of keratinocytes, melanocytes, Langerhans cells, and Merkel cells in five layers. Under the epidermis is the dermis having a thickness of 0.3 mm (eyelids) to 3 mm (back), primarily comprising collagen, elastic fibers and extrafibrillar matrix in two layers, the upper papillary layer and the lower reticular layer. Under the dermis is the hypodermis housing large blood vessels and nerves primarily comprising fibroblasts, adipose cells, and macrophages.

It is often desired to remove unsightly blemishes on the skin of an animal. In some instances there is a medical reason for removing such blemishes, for example to remove warts or precancerous growths. That said, often it is desired to remove or reduce the extent of a skin blemish for exclusively cosmetic reasons.

In the art, it is known to remove skin blemishes by damaging the skin or the blemish and the letting the skin heal. The thus-rejuvenated skin is often devoid of the blemish or the extent of the blemish is somewhat reduced. Methods for damaging the skin to remove blemishes include peeling with abrasives (e.g., ground cherry or olive pits), peeling with chemical solutions (e.g., including phenol, trichloroacetic acid or alpha hydroxy acids) or ablation by heating (e.g., with electromagnetic radiation such as from a laser) to remove blemishes such as acne scars, wrinkles, fine lines age spots, uneven skin tone, pigmentation, large pores and the like.

It has been found that in some instances improved results are achieved when, instead of damaging a large contiguous area of skin, many small areas of the skin are damaged and allowed to heal, a technique known as fractional technology. It is believed that the body can more easily heal a small damaged area surrounded by healthy tissue then a large damaged area. Further, as in fractional technology the area of the damaged skin is relatively small, it becomes possible to damage the area of skin more deeply, leading to more effective treatments of blemishes as well as a greater skin-rejuvenating effect, attributed to more effective stimulation of new collagen growth. In some instances, a fractional technology treatment must be repeated a number of times in the same area of skin to achieve maximal desired effect.

One typical implementation of fractional technology is fractional laser therapy (e.g., using the Pixel Perfect™ by Alma Lasers Ltd., Caesaria, Israel) where a laser beam is directed at an area of skin to produce a large number of small perforations (e.g., 49 perforation/$cm^2$, each perforation about 0.2 mm diameter). Such treatment has been shown to be effective in stimulating new collagen and blood vessel development, improving skin texture and tone as well as removing fine lines, wrinkles, acne scars and uneven pigmentation. Similar devices have been described, for example, in PCT Patent Publication WO 2008/083305.

One typical implementation of fractional technology is based on mechanical damage to the skin, for example using the Dermaroller(r) (available from Dermaroller s.a.r.l, Friesenheim, France), a needle-studded roller that, when rolled over a skin surface, physically pierces the skin with about 250 punctures/$cm^2$ to a depth of 0.3 mm to 1.5 mm. Such treatment is alleged to stimulate new collagen and blood vessel development, to remove wrinkles, reduce hyper pigmentation, striae, acne scars and bum scars.

Although known methods of dermatological treatment are often effective, there is an ongoing need to improve such treatments. For some blemishes such as deep pigmentation blemishes, known dermatological treatment methods are not insufficiently effective.

SUMMARY OF THE INVENTION

According to an aspect of some embodiments of the invention there is provided, a method of dermatological treatment of an area of skin of a subject, comprising:

a) on an area of skin of a subject, contacting a plurality of cooling probes, each having a distal end with a distal tip; and b) maintaining the plurality of cooling probes in contact with the area of skin for a period of time while the distal ends of the plurality of cooling probes are at a probe temperature of not more than about 5° C. so as to substantially cool a volume of tissue, wherein during the maintaining of the cooling probes in contact with the area of skin, the distance between distal tips of two neighboring cooling probes is not more than about 10 mm, thereby providing a beneficial effect as a result of the substantial cooling of the volume of tissue. In some embodiments, the subject is a human. In some embodiments, the subject is a non-human animal.

In some embodiments, the beneficial effect is at least partially caused by cold damage to portions of the substantially cooled volume of tissue. In some embodiments, the treatment is for skin rejuvenation and the beneficial effect is an improved appearance of the area of skin.

In some embodiments, the beneficial effect is at least partially caused by cold damage to at least some melanocytes in the substantially cooled volume of tissue. In some embodiments, the treatment is for skin lightening and the beneficial effect is lightening the color of the area of skin. In some embodiments, the treatment is for treating a pigmentation blemish of the skin and the beneficial effect is reducing the severity of the pigmentation blemish.

In some embodiments, the beneficial effect is at least partially caused by cold damage to at least some adipocytes in the substantially cooled volume of tissue. In some embodiments, the treatment is for reducing the effect of undesired adipocytes and the beneficial effect is reducing the volume of fat under the area of skin.

According to an aspect of some embodiments of the invention there is also provided, a dermatological treatment device comprising: a plurality of cooling probes, each cooling probe having a distal end with a distal tip configured to contact skin of a subject, where each cooling probe is configured to allow cooling of a respective distal end; and the cooling probes configured so that when the plurality of cooling probes contacts skin of a subject, the distance between distal tips of two neighboring cooling probes is not more than about 10 mm.

In some embodiments, the cooling probes are configured to be arranged in an array when contacting the skin of a subject.

In some embodiments, a cooling probe is configured for non-penetrating surface contact with skin of a subject, where the distal tip contacts the surface of skin of a subject.

In some embodiments, a cooling probes is configured for penetrating contact with skin of a subject. In some embodiments, a cooling probe is configured to pierce the skin of a subject to make penetrating contact.

In some embodiments, the device is portable.

Unless otherwise defined, all technical and scientific terms used herein have the same meaning as commonly understood by one of ordinary skill in the art to which the invention pertains. In case of conflict, the specification, including definitions, will control.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

BRIEF DESCRIPTION OF THE DRAWINGS

The invention will now be described further, by way of example, with reference to the accompanying drawings, in which:

FIGS. 1A, 1B and 1C are schematic depictions of an embodiment of a device as described herein including a plurality of cooling probes configured for non-penetrating surface contact with skin;

DETAILED DESCRIPTION OF THE PREFERRED EMBODIMENT(S)

Figure 2A:
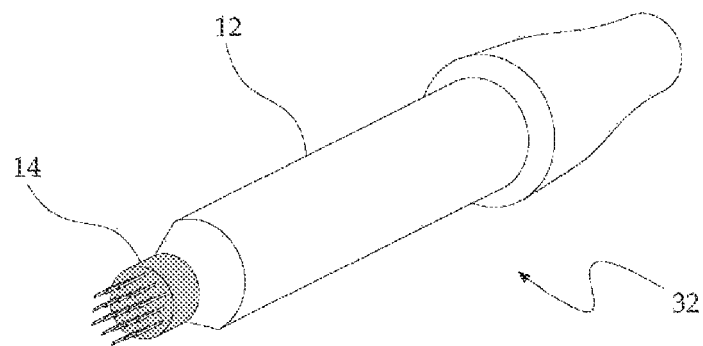
FIGS. 2A, 2B and 2C are schematic depictions of an additional embodiment of a device as described herein including a plurality of cooling probes arranged in a hexagonal array configured for piercing skin and making penetrating contact with skin.

The invention, in some embodiments, relates to the field of dermatological treatment, and more particularly, but not exclusively, to methods and devices for dermatological treatment.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

Cryotherapy is generally known for immediate radical destruction of large volumes of tissue, e.g., warts, the uterine lining, tumors and whole organs such as the prostate. Although temperatures as warm as −40° C. are considered by some to be sufficient to destroy tissue, in typical cryotherapy extreme cold (e.g., −196° C. with liquid nitrogen or a cryotherapy probe) is directly applied to a desired volume of tissue at a rate far greater than can be warmed by the body to cause very rapid cooling to a very low temperature, leading to immediate indiscriminate death of all cells in the tissue volume. In some cryotherapy modes, cooling is applied for a relatively long period of time so that an ice front propagates outwards from a cryotherapy probe, forming an expanding "ice ball" of destroyed tissue.

Dermatological cryotherapy usually involves direct application of a cryogenic liquid such as liquid nitrogen or direct contact with a cryogenic surface (e.g., using a Cryopen(r) by CryoPen Inc, Corpus Christi Tex., USA). Such methods are effective for indiscriminately destroying a volume of exposed tissue such as warts, tumors and the like.

Dermatological cryotherapy is not suitable for many applications, especially cosmetic applications, due to the extent and depth of tissue damage caused, potentially leading to scarring. The physical border of tissue damage is difficult to control as the ice ball of destroyed tissue advances in all direction, both radiating outwards on the surface of the skin and advancing inwards into the body, often deeper than desirable. The difficulty in controlling the depth of tissue destruction is aggravated by the fact that different tissue types have a different thermal conductance. Additionally, some cell types are more sensitive to cold than others often leading to unpredictable results. For example, melanocytes are relatively sensitive to cold, so an unwanted side effect of dermatological cryotherapy is an unsightly lightening of the skin surrounding the area of destroyed tissue.

According to an aspect of the teachings herein, there is provided a method of dermatological treatment of an area of skin of a subject, comprising:

a) on an area of skin of a subject, contacting a plurality of cooling probes, each having a distal end with a distal tip; and b) maintaining the plurality of cooling probes in contact with the area of skin for a period of time while the distal ends of the plurality of cooling probes are at a probe temperature of not more than about 5° C. so as to substantially cool a volume of tissue, wherein during the maintaining of the cooling probes in contact with the area of skin, the distance between distal tips of two neighboring cooling probes is not more than about 10 mm, thereby providing a beneficial effect as a result of the substantial cooling of the volume of tissue. In some embodiments, the subject is a human. In some embodiments, the subject is a non-human animal.

In contrast to known applications of dermatological cryotherapy, in some embodiments of the methods of dermatological treatment described herein, heat is removed from body tissue at a comparatively moderate rate and/or to a relatively high temperature due to one or more reasons that, depending on the embodiment, may include, inter alia, one or more of relative high cooling probe temperature, relatively small contact area (between the cooling probes and tissue), relatively slow heat transfer through long and narrow cooling probes and relatively low heat-capacity of cooling probes. As a result, the body of the subject is able to at least partially compensate for the cooling caused by the cooling probes, especially in tissue that is not directly contacting the cooling probes. As a result, in some embodiments the volume of tissue substantially cooled is localized to a volume defined by the positioning of the cooling probes on the skin. As a result, in some embodiments, the temperature to which the volume of tissue is cooled is relatively high. As a result, in some embodiments, the effect of the application of cooling is controllably localized and unwanted damage to tissue remote from the distal end of the cooling probes is avoided.

In some embodiments, the area of skin contacted by the plurality of cooling probes has the shape of a closed curve, that is to say, the area of skin has a shape defined by the point of contact of at least three of the plurality of cooling probes that are located at the edges of the area of skin, optionally with one or more probes having a point of contact inside the area of the skin.

The area of skin can be of any suitable size. In some embodiments, the area of skin is at least about 1 cm$^2$, at least about 2.25 cm$^2$, at least about 4 cm$^2$ and in some embodiments even at least about 6.4 cm$^2$.

The area of skin can have any suitable shape, e.g., a square, a rectangle, a triangle, a circle an oval. The cooling probes can be arranged in any suitable way within the area of skin. That said, in some embodiments, it is convenient to arrange the cooling probes in a regular pattern so that the cooling of the volume of tissue is relatively homogenous. Accordingly, in some embodiments, the cooling probes are arranged in an array comprising rows and columns so that each non-edge cooling probe has four substantially equidistant nearest neighbors arranged in a cross-pattern. Typical such arrays are a square array of 2×2 (total 4 cooling probes), 3×3 (total 9 cooling probes), 4×4 (total cooling 16 probes), 5×5 (total 25 cooling probes) and so on, or a rectangular array such as 2×3 (total 6 cooling probes), 3×5 (total 15 cooling probes), 4×6 (total 24 probes), 5×7 (total 35 cooling probes) and so on. In some embodiments, the cooling probes are arranged in a hexagonal array so that each non-edge cooling probe has 6 substantially equidistant nearest neighbors. Typical such hexagonal arrays include 7 cooling probes (one non-edge cooling probe), 19 cooling probes (7 non-edge cooling probes) and 37 cooling probes (19 non-edge cooling probes).

Clearly, the volume of tissue that is substantially cooled is also defined by a depth dimension. As is discussed herein, in some embodiments the cooling probes penetrate into the skin. Thus, in some embodiments, the volume of tissue substantially cooled is defined by the area of skin defined by the probes (having borders somewhat outside the area defined by the contact points of the cooling probes) and the depth which the probes penetrate into the skin (having a border somewhat deeper than the depth to which the distal tips of the cooling probes penetrate).

The importance of controllability cannot be dismissed, especially as when the method described herein is applied to cosmetic dermatology. The physical and thermal properties (e.g., thickness, heat conductivity, sensitivity) of skin varies dramatically depending on such factors as location on the body, age of the subject, skin color, thickness, skin type (e.g., greasy or dry) and history (tanning, smoking, acne scarring, make-up use). Embodiments of the method disclosed herein allow the operator performing the method (e.g., a cosmetician, skin-technician, and in some embodiments medical personnel) to adjust the intensity of treatment (e.g., length of period of time the cooling probes are maintained in contact with the area of skin, the probe temperature, the number and arrangement of probes making up the plurality of probes) to the skin of the subject. In some embodiments, the operator performs an initial treatment under moderate (relatively little cooling for a relatively short time) and optionally repeats the treatment while progressively increasing the intensity of the treatment until an intensity of treatment is found that provides good results without causing irreversible damage that potentially occurs with uncontrolled methods such as known in the art.

In some embodiments, the volume of tissue near and between the distal ends of the cooling probes is cooled at a modest rate to a relatively high temperature for a relatively long time with more intense cooling only in a relatively small volume of tissue localized around or actually contacting a surface of the cooling probes. As a result, some embodiments described herein are exceptionally suitable for certain types of dermatological treatments. For example, in some embodiments, the cooling has an effect similar to fractional technology where inside a large volume of tissue, many small sub-volumes of tissue are damaged, so that each damaged sub-volume of tissue is surrounded by undamaged tissue, leading to quick healing and a rejuvenating effect. For example, in some embodiments, the cooling has a selective effect where cold-sensitive cells (e.g., melanocytes or adipocytes) are more adversely affected (e.g., selectively killed or damaged) than surrounding cells (e.g., keratinocytes).

In some embodiments, the volume of tissue substantially cooled comprises tissue of the epidermis. In some embodiments, the volume of tissue substantially cooled comprises tissue of the dermis. In some embodiments, the volume of tissue substantially cooled comprises tissue of the hypodermis.

In some embodiments, the treatment is a medical treatment. In some embodiments, the treatment is a non-medical cosmetic treatment. In some embodiments, the treatment is an elective non-medical cosmetic treatment, for example, treatment of a superficial or non-superficial skin blemish.

In some embodiments, the beneficial effect of the method is at least partially caused by cold damage to portions of the substantially cooled volume of tissue.

For example, in some embodiments, the treatment is for skin rejuvenation and the beneficial effect is an improved appearance of the area of skin. Such embodiments, include treatment of damaged skin, sun-damaged skin, aged skin, wrinkled skin, blemished skin, scarred skin including acne scars and treatment of large skin pores. In some such embodiments, the cold damage stimulates beneficial healing processes, in some embodiments including collagen formation. Physical damaging techniques (e.g., perforation with a Dermaroller(r)) are limited: if the needles are too big or too densely packed, the treatment is unbearably painful, but if the needles are too small or too spaced apart, the damage caused is insufficient for optimal effect. In some embodiments of the method described herein, the actual contact by the cooling probes causes moderate, little or no discomfort, but subsequent cooling leads to additional damage (e.g., cold damage or freeze damage proximal to the cooling probes). The discomfort caused by the damage is reduced by the numbing effect of the cooling. Additionally, although not wishing to be bound to any one theory, it is hypothesized that cooling triggers or stimulates certain cellular responses that during the subsequent healing process leads to an improved external appearance, for example due to new skin growth and an unexpected stimulation of collagen generation.

Thus, according to the teachings herein, there is also provided a method for improving the appearance of an area of skin (skin rejuvenation) by damaging selected portions of the area of the skin, substantially as described herein.

Melanocytes are known as being relatively sensitive to cold, dying at temperatures where other skin components, e.g., keratinocytes or the fibrocollagenous matrix, are substantially unaffected. Thus, in some embodiments, the beneficial effect is at least partially caused by cold damage to at least some melanocytes in the substantially cooled volume of tissue.

In some such embodiments, the treatment is for skin lightening and the beneficial effect is lightening of the color of the area of skin, for example by adversely effecting (e.g., killing) at least some melanocytes in the substantially cooled volume of tissue. In some such embodiments, lightening is only of a localized area, e.g., due to the presence of a darker discoloration. In some embodiments, lightening is of an extensive area of skin, e.g., due to a desire to have a lighter skin shade. In such embodiments, different small areas of the skin are treated at separate times as opposed to the entire body surface being treated simultaneously. In some such embodiments, a volume of tissue is cooled so as to adversely effect only a limited percentage of melanocytes, so that in a single treatment there is only a relatively slight lightening of skin. The treatment is then optionally repeated, e.g., at a later date, so that the exact degree of skin lightening and the desired skin color is achieved.

Thus, according to the teachings herein, there is also provided a method for skin lightening by adversely affecting melanocytes in an area of skin, substantially as described herein.

In some such embodiments, the treatment is for treating a pigmentation blemish of the skin and the beneficial effect is reducing the severity of the pigmentation blemish, for example by adversely effecting (e g , killing) at least some melanocytes in the substantially cooled volume of tissue. Typical such pigmentation blemishes include hyper-pigmentation, freckles, birthmarks, liver spots and pigmentation blemishes such as melasma. In some embodiments a pigmentation blemish is a superficial blemish or a blemish in the epidermis. e.g., a liver spot, birthmark or freckles. In some embodiments a pigmentation blemish is a blemish in the dermis, e.g., deep pigmentation blemishes such as melasma.

Thus, according to the teachings herein, there is also provided a method for treating skin by adversely affecting melanocytes in an area of skin, substantially as described herein. In some embodiments, the melanocytes are melanocytes found in the dermis. In some embodiments, the melanocytes are melanocytes found in the epidermis.

Adipocytes are known as being relatively sensitive to cold, being adversely effected at temperatures where other skin components are substantially unaffected. Thus, in some embodiments, the beneficial effect is at least partially caused by cold damage to at least some adipocytes in the substantially cooled volume of tissue. In some such embodiments, the treatment is for reducing the effect of undesired adipocytes and the beneficial effect is reducing the volume of fat in or under the area of skin, in some embodiments, adipocytes in the hypodermis.

As discussed in the introduction above, the hypodermis (about 3 to 5 mm below the surface of the skin) includes adipocytes. Methods and devices for destruction of adipocytes with the aid of low temperatures have been described in the PCT Patent Publication WO 2008/055243 to Zeltiq Aesthetics, Inc. (Pleasanton Calif., USA). Therein: probes are inserted into a layer of fat and cooled to an extent that damages adipocytes without substantial damage to other cells. In such a way, the volume of the fat layer is reduced. Therein, sufficient technical details for implementing the method are lacking.

Thus, according to the teachings herein, there is also provided a method for treating skin by adversely affecting adipocytes in an area of skin, substantially as described herein. In some embodiments, the method is applied to treatment of cellulite. In some embodiments, the method is implemented for body sculpting.

In some embodiments, the contact of the cooling probes with the skin is a non-penetrating surface contact, so that during the maintaining contact of the cooling probes with the area of the skin, the distal tips of the cooling probes contact the skin surface. In some such embodiments, the distal tips of the cooling probes are configured for non-penetrating surface contact, e.g., are convex or flat. Such embodiments are exceptionally useful, for example, for treating superficial skin blemishes, for lightening the skin or for improving the appearance of the area of skin, where the damage to the skin is caused by the cooling.

In some embodiments, the contact of the cooling probes with the skin is penetrating contact, so that during the maintaining contact, the distal ends of the cooling probes penetrate into the epidermis of the skin so that at least the distal tips are positioned inside the skin. In some embodiments, prior to the actual piercing of the skin, a lubricant material (e.g., glycerol, silicone oil) is applied to the outer surface of the distal ends of the cooling probes. In some such embodiments, the cooling probes are configured to pierce the skin, e.g., the distal ends are sufficiently rigid and the distal tips are pointed. In some such embodiments, penetrating contact allows substantial cooling of a volume tissue at a depth from the surface of the skin. In some such embodiments, the volume of tissue substantially cooled comprises tissue of the epidermis (typically to about 1 mm from the surface of the skin). In some such embodiments, the volume of tissue cooled comprises tissue of the dermis (typically to about 2 mm from the surface of the skin). In some such embodiments, the volume of tissue cooled comprises tissue of the hypodermis (typically from about 2 mm to from about 3 mm from the surface of the skin).

Depending on the depth into the skin to which the distal tips penetrate, such embodiments are exceptionally useful, for example, for treating superficial skin blemishes, for lightening the skin, for treating skin blemishes caused by melanocytes in the epidermis or dermis, and for effecting adipocytes. Additionally, such embodiments are exceptionally useful for for improving the appearance of the area of skin, where the damage to the skin is caused by both the cooling and the physical damage caused by penetrating into the skin.

In some embodiments, during the maintaining contact, the distal tips penetrate at least about 0.2 mm into the skin.

In some embodiments, during the maintaining contact, the distal tips penetrate not more than about 0.5 mm, not more than about 1 mm, not more than about 2 mm, not more than about 2.5 mm and even not more than about 4 mm from the skin surface.

In some such embodiments, during the maintaining contact, the distal tips are positioned inside the epidermis of the skin. Although the thickness of the epidermis varies, in typical such embodiments the distal tips are positioned between about 0.25 mm and about 1 mm from the skin surface.

In some such embodiments, during the maintaining contact, the distal tips are positioned inside the dermis of the skin. Although the depth where the dermis is located varies, in typical such embodiments the distal tips are positioned between about 1 mm and about 2.5 mm from the skin surface. Some such embodiments are exceptionally useful for treating deep pigmentation blemishes caused by melanocytes such as melasma.

In some such embodiments, during the maintaining contact, the distal tips are positioned inside the hypodermis of the skin. Although the depth where the hypodermis begins varies, in typical such embodiments the distal tips are positioned between about 2 mm and about 1 mm from the skin surface. Some such embodiments are exceptionally useful for adversely effecting adipocytes, for example for body sculpting or treating cellulite.

In some embodiments, the cooling probes are contacted with the area of skin serially. In typical such embodiments, each cooling probe of the plurality of cooling probes is provided as a separate unit that is contacted with the area of skin individually.

In some embodiments, at least two of the cooling probes and in some embodiments all of the cooling probes of the plurality of cooling probes are contacted with the area of skin substantially simultaneously. In typical such embodiments, the at least two and even the entire plurality of cooling probes are provided as a single cooling-probe assembly.

In some embodiments, the plurality of cooling probes comprises at least four cooling probes. In some embodiments, the plurality of cooling probes comprises at least eight, at least twelve, at least twenty and even at least thirty cooling probes.

As noted above, in some embodiments, during the maintaining of contact of the plurality of the cooling probes with the area of skin, the distance between distal tips of two neighboring cooling probes is not more than about 10 mm. In some embodiments, during the maintaining of contact the distance between distal tips of two neighboring cooling probes is not more than about 4 mm, not more than about 3 mm and even not more than about 2 mm.

Generally, in embodiment of the method it is desirable that a significant portion of the area of skin is not in direct contact with the cooling probes so that between any two damaged volumes of tissue there is undamaged tissue. Thus, in some embodiments, during the maintaining of contact of the plurality of the cooling probes with the area of skin, not more than 50%, not more than 40%, not more than 30% and even not more than 30% of the area of skin is occupied (in contact) with the cooling probes.

In some embodiments, during the maintaining of contact of the plurality of the cooling probes with the area of skin, the area of skin is in contact with at least about 4 cooling probes per $cm^2$, at least about 8 cooling probes per $cm^2$, at least about 16 cooling probes per $cm^2$, and even at least about 20 cooling probes per $cm^2$.

In some embodiments, the cooling probes of the plurality of cooling probes are substantially identical. In some embodiments, at least two of the cooling probes of the plurality of cooling probes are physically different one from the other. The shape (in cross section perpendicular to the distal end) of the distal tip and of the distal end of a cooling probe is any suitable shape, for example, substantially circular, ovoid, substantially square, substantially rectangular. That said, in some embodiments where the cooling probes are configured to pierce skin the shape of the distal end is substantially circular to reduce the chance of tearing skin.

As noted above, in some embodiments, the distal tips of the cooling probes are configured for non-penetrating surface contact with skin. For example, in some such embodiments, the distal tips are convex or flat. In some such embodiments, the cross sectional area of the distal tip of a cooling probe configured to make contact with the skin is not more than about 3.14 mm2 (equivalent to diameter of 2 mm round cross section distal tip), not more than about 0.79 mm2 (equivalent to diameter of 1 mm round cross section distal tip), not more than about 0.5 mm2 (equivalent to diameter of 0.8 mm round cross section distal tip), and even not more than about 0.2 mm2 (equivalent to diameter of 0.5 mm round cross section distal tip).

As noted above, in some embodiments, the distal ends of the cooling probes are configured for piercing skin, e.g., the distal ends are sufficiently rigid and/or the distal ends taper to define a sharpened (e.g., beveled) distal tip. In some such embodiments, a distal end of a cooling probe has a cross-sectional area of not more than about 3.14 mm2 (equivalent to diameter of 2 mm round cross section cooling probe), not more than about 0.79 mm2 (equivalent to diameter of 1 mm round cross section cooling probe), not more than about 0.5 mm2 (equivalent to diameter of 0.8 mm round cross section cooling probe) and even not more than about 0.2 mm2 (equivalent to diameter of 0.5 mm round cross section cooling probe). It is important to note that, in some embodiments, it is preferred that a distal end of a cooling probe has a cross-sectional area of not more than about 0.5 mm2 (equivalent to diameter of 0.8 mm round cross section cooling probe) due to the reduced pain during the actual piercing of the skin. In this context, it is important to note that acupuncture needles have a diameter of between about 0.5 and 0.18 mm.

In some embodiments, the proximal ends of the cooling probes are functionally associated with a heat sink that is contacted with a cooling material (e,.g, a solid such as dry ice or a fluid such as liquid nitrogen) and the temperature of the distal end and distal tip of the cooling probe is lowered through heat conduction through a solid material making up the cooling probes.

In some embodiments, the proximal ends of the cooling probes are functionally associated with a cooling generator (e.g., in contact with a heat sink of a cooling generator) and the temperature of the distal end and distal tip of the cooling probe is lowered through heat conduction through a solid material making up the cooling probes. In some embodiments, the cooling probes include channels to accommodate the flow of a cooling fluid and the distal ends of the cooling probes are cooled by the passage of the cooling fluid through the channels, for example as discussed in U.S. Pat. No. 6,503,246.

In some embodiments, the distal ends of the plurality of cooling probes are at the reduced probe temperature prior to the contact with the area of skin. Some such embodiments include embodiments where the contact is non-piercing contact.

In some embodiments, the distal ends of the plurality of cooling probes are cooled to the reduced probe temperature during the period of time the cooling probes are maintained in contact with the area of skin. Some such embodiments include embodiments where the contact is piercing contact. In some such embodiments, the distal ends are cooled to the reduced probe temperature subsequent to the cooling probes piercing the skin and positioned at the desired depth inside the skin.

As noted above, in some embodiments the distal ends of the cooling probes are at a probe temperature of not more than about 5° C. so as to substantially cool the volume of tissue. As the distal tips are in contact with warm human tissue during the maintaining, and as in some embodiments the heat transfer capacity of the cooling probes is very limited, by "probe temperature" is not necessarily meant the actual temperature of the distal end at a given moment in time, but rather the temperature that the distal end would attain if maintained in air at standard temperature and pressure.

During the maintaining of contact of the plurality of cooling probes with the area of skin, the probe temperature is at any suitable probe temperature to cause the desired beneficial effect. That said, in some embodiments, a lowest probe temperature during the maintaining is not less than about −5° C., not less than about −10° C. and even not less than about −20° C. That said, in some embodiments, a lowest probe temperature during the maintaining is not more than about 1° C., not more than about −5° C., not more than about −10° C., not more than about −20° C., not more than about −30° C., not more than about −40° C., and even not more than about −50° C. That said, in some embodiments, a lowest probe temperature during the maintaining is as low as that of liquid nitrogen, −196° C.

The period of time that the plurality of cooling probes is maintained in contact with the area of skin is any suitable period of time to cause the desired beneficial effect. That said, in some embodiments, the period of time is not less than about 1 second, not less than about 3 seconds, not less than about 5 seconds, not less than about 10 seconds, not less than about 30 seconds, not less than about 2 minutes, not less than about 4 minutes, not less than about 10 minutes, and even not less than about 15 minutes. That said, in some embodiments, the period of time is not more than about 1 second, not more than about 3 seconds, not more than about 5 seconds, not more than about 10 seconds, not more than about 30 seconds, not more than about 2 minutes, not more than about 4 minutes, not more than about 10 minutes, not more than about 15 minutes and even not more than about 60 minutes.

In some embodiments where the contact is piercing contact, the distal tips of the cooling probes are cooled to a temperature sufficient to reduce a feeling of discomfort when the cooling probes pierce the skin prior to piercing the skin and being positioned at the desired depth inside the skin. Subsequently, the distal ends are cooled to the reduced probe temperature subsequent to the cooling probes piercing the skin.

In some embodiments, during the period of time of maintaining contact, the intensity of cooling of the cooling probes is maintained substantially constant. In some embodiments, during the period of time of maintaining contact with the period of skin, the intensity of cooling of the cooling probes is varied, so that in some embodiments the temperature of the distal ends of the cooling probes fluctuates.

In some embodiments, the cooling of the volume of tissue is such that substantially no tissue is frozen, but cooled to a temperature that leads to a beneficial effect.

In some embodiments, the cooling of the volume of tissue is such that only tissue in direct contact with a surface of the distal ends of the cooling probes is frozen.

In some embodiments, the cooling of the volume of tissue is such that a substantial portion of the substantially cooled volume of tissue is frozen.

In some embodiments, substantially the entire substantially cooled volume of tissue is homogeneously affected by the application of cold. Such embodiments are useful, for example, for homogeneously affecting melanocytes in the volume of tissue.

In some embodiments, only some (the tissue directly contacting or in the near vicinity of the cooling probes) of the substantially cooled volume of tissue is affected by the application cold. Such embodiments are useful, for example, for generating loci of damaged tissue surrounded by healthy tissue.

The method described herein may be implemented using any suitable device. In some embodiments, a method as described herein is implemented using a dermatological device as described herein.

According to the an aspect of some embodiments, there is provided a dermatological treatment device comprising: a plurality of cooling probes, each the cooling probe having a distal end with a distal tip configured to contact skin of a subject, where each cooling probe is configured to allow cooling of a respective the distal end; and the cooling probes configured so that when the plurality of cooling probes contacts skin of a subject, the distance between distal tips of two neighboring cooling probes is not more than about 10 mm.

In some embodiments, the cooling probes are configured so that when the plurality of cooling probes contacts skin of a subject the distance between distal tips of two neighboring cooling probes is not more than about 4 mm, not more than about 3 mm and even not more than about 2 mm.

In some embodiments, the plurality of cooling probes comprises at least four cooling probes, at least eight, at least twelve, at least twenty and even at least thirty cooling probes.

In some embodiments, the cooling probes are configured so that when the plurality of cooling probes contacts skin of a subject, there are at least about 4 cooling probes per $cm^2$, at least about 8 cooling probes per $cm^2$, at least about 16 cooling probes per $cm^2$, and even at least about 20 cooling probes per $cm^2$ skin. In some embodiments, such configuration includes that the cooling probes are secured to a cooling-probe base, for example to constitute a unitary cooling-probe assembly, as described hereinbelow.

In some embodiments, the cooling probes are configured so as to allow the plurality of cooling probes to contact an area of skin of a certain size. In some embodiments, the area of skin is at least about 1 $cm^2$, at least about 2.25 $cm^2$, at least about 4 $cm^2$ and in some embodiments even at least about 6.4 $cm^2$. In some embodiments, such configuration includes that the cooling probes are secured to a cooling-probe base, for example to constitute a unitary cooling-probe assembly, as described hereinbelow.

In some embodiments, the cooling probes are configured so that during the maintaining of contact of the plurality of the cooling probes with the area of skin, not more than 50%, not more than 40%, not more than 30% and even not more than 30% of the area of skin is occupied (in contact) with the cooling probes. In some embodiments, such configuration includes that the cooling probes have a sufficiently small diameter (are thin enough) and sufficiently spaced-apart (if secured to a cooling-probe base, for example to constitute a unitary cooling-probe assembly, as described hereinbelow).

In some embodiments, the cooling probes are configured to be arranged on the skin so as to define an area having a certain shape. Typical shapes include square, rectangular, triangular, circular and oval. In some embodiments, such configuration includes that the cooling probes are secured to a cooling-probe base, as described hereinbelow.

In some embodiments, the cooling probes are configured to be arranged on the skin in a certain way. In some embodiments, such configuration includes that the cooling probes are secured to a cooling-probe base, as described hereinbelow. In some embodiments, the cooling probes are configured to be arranged in an array when contacting the skin of a subject. In some embodiments, the cooling probes are configured to be arranged in an array comprising rows and columns so that the each non-edge cooling probe has four substantially equidistant nearest neighbors arranged in a cross-pattern. Typical such arrays are square of 2×2, 3×3, 4×4, 5×5 and so on, or rectangular such as 2×3, 3×5, 4×6, 5×7 and so on. In some embodiments, the cooling probes are configured to be arranged in a hexagonal array so that each non-edge cooling probe has 6 substantially equidistant nearest neighbors. Typical such hexagonal arrays include 7 cooling probes, 19 cooling probes and 37 cooling probes.

In some embodiments, all the cooling probes of the plurality of cooling probes are substantially identical. In some embodiments, at least two of the cooling probes of the plurality of cooling probes are physically different one from the other.

The shape (in cross section perpendicular to the distal tip) of the distal end of a cooling probe is any suitable shape, for example, substantially circular, ovoid, substantially square, substantially rectangular and is typically chosen based on factors such as providing uniform cooling of tissue and ease of manufacture. That said, in some embodiments where the cooling probes are configured to pierce skin, the shape of the distal end is substantially circular to reduce the chance of tearing skin.

In some embodiments, a cooling probe is configured for non-penetrating surface contact with skin of a subject, where the distal tip contacts the surface of skin of a subject. In some such embodiments, the distal tips of the cooling probes are configured for non-penetrating surface contact, e.g., are convex or flat. The shape of the distal tip of a cooling probes (in cross section) is any suitable shape, e.g., triangle, square, hexagonal, oval, or circular. In some such embodiments, the cross sectional area of the distal tip of a cooling probes configured to make contact with the skin is not more than about 3.14 mm2 (equivalent to diameter of 2 mm round cross section distal tip), not more than about 0.79 mm2 (equivalent to diameter of 1 mm round cross section distal tip), not more than about 0.5 mm2 (equivalent to diameter of 0.8 mm round cross section distal tip), and even not more than about 0.2 mm2 (equivalent to diameter of 0.5 mm round cross section distal tip).

In some embodiments, a cooling probe is configured for penetrating contact with skin of a subject, for example the distal end is sufficiently rigid and/or the distal tip is configured to pierce skin, e.g., the distal ends taper to define a sharpened (e.g., beveled) distal tip. In some such embodiments, the distal end of the cooling probes is elongated. In some such embodiments, the outer surface of the distal end is provided with a lubricious coating allowing easier passage through the skin. In some such embodiments, a distal end of a cooling probe has a cross-sectional area of not more than about 3.14 mm2 (equivalent to diameter of 2 mm round cross section cooling probe), not more than about 0.79 mm2 (equivalent to diameter of 1 mm round cross section cooling probe), not more than about 0.5 mm2 (equivalent to diameter of 0.8 mm round cross section cooling probe) and even not more than about 0.2 mm2 (equivalent to diameter of 0.5 mm round cross section cooling probe). It is important to note that, in some embodiments, it is preferred that a distal end of a cooling probe has a cross-sectional area of not more than about 0.5 mm2 (equivalent to diameter of 0.8 mm round cross section cooling probe) due to the reduced pain during the actual piercing of the skin.

In some embodiments, the cooling probes are configured to penetrate to any suitable depth in the skin which, as described above, is dependent on the nature of the treatment to be applied on on the nature of the skin of the subject.

In some embodiments, a cooling probe is configured to penetrate into skin so that the distal tip is located inside the hypodermis, generally up to about 25 mm, but more typically not more than about 12 mm, and even not more than about 8 mm.

In some embodiments, a cooling probe is configured to penetrate into skin so that the distal tip is located inside the dermis, up to about 2 mm, but more typically not more than about 1.5 mm.

In some embodiments, a cooling probe is configured to penetrate into skin so that the distal tip is located inside the epidermis, up to about 1 mm, but more typically not more than about 0.5 mm In some embodiments, a cooling probe is configured to penetrate to between about 0.5 mm and about 25 mm into the skin. In this context it is interesting to note that in the art of acupuncture, needles typically penetrate from about 6 mm to about 25 mm into the subject.

In some embodiments, a cooling probe is configured to penetrate to no more than about 3 mm, that is considered long enough so that the distal tip of the cooling probe just enters the hypodermis.

In some embodiments, a cooling probe is configured to penetrate to no more than about 2 mm, that is considered long enough so that the distal tip of the cooling probe enters the dermis.

In some embodiments, a cooling probe is configured to penetrate to no more than about 1.5 mm, a penetration depth into the dermis similar to that of the Dermaroller(r).

In some embodiments, a cooling probe is configured to penetrate to no more than about 1 mm, considered long enough so that the distal tip of the cooling probe just enters the dermis.

In some embodiments, the device includes a penetration stop, a physically component limiting the depth of penetration of a cooling probe. In some embodiments, a penetration stop is a component of a cooling probe, such as "shoulders" or a broadening that functions to limit the depth of penetration of the cooling probe. In some embodiments, a penetration stop is not a component of a cooling probe.

In some embodiments, a cooling probe is configured to allow substantial cooling of tissue only at the distal tip of the distal end, for example, an elongated distal end of a cooling probe is covered with a thermally insulating layer (e.g., PTFE) excepting at an exposed distal tip. In cooling probes configured for non-piercing surface contact such configuration allows substantial cooling only at the distal tip allows more accurate application of cold to tissue. In cooling probes configured for penetrating contact such configuration allows substantial cooling only at a desired depth allowing for fewer side effects, for example, allowing damaging deep cells with cold (e.g., hypodermal adipocytes), while avoiding exposure of less deep cells (e.g., epidermal melanocytes) in such a way eliminating adipocytes without causing skin discoloration.

In some embodiments, a distal end of a cooling probe comprises channels to accommodate the flow of a cooling fluid. In such embodiments where the cooling probe is configured for piercing skin, the cooling probe has a relatively large diameter such as described in U.S. Pat. No. 6,503,246. In some such embodiments configured for making non-penetrating surface contact with the skin, the cooling probe has a relatively small diameter but is fragile and therefore not suitable for piercing skin. In any case, such embodiments are relatively expensive, complex to use and maintain, and inconvenient due to the required tubing, seals, pumps, cooling fluid supply and the like required for operation. Further, in many embodiments, such cooling probes are impractical or impossible to implement, for example where the plurality of cooling probes comprises relatively many cooling probes (e.g., more than four cooling probes) and/or where two probes must be placed close together (e.g., closer than 10 mm) and/or where the concentration of probes per surface area is relatively high.

In some embodiments, a cooling probe is configured to transfer heat from the distal end of the cooling probe (that contacts the area of skin) to a proximal end of the cooling probe by heat transfer through the solid material. e.g., the cooling probe is substantially of a solid material. In some such embodiments, the cooling probe is devoid of channels for the flow of cooling fluid, allowing the diameter of the cooling probe to be relatively small and allowing for simple and cheap construction without requiring the complex tubing, seals and the like. Due to the simplicity and compactness, embodiments that require a large number of cooling probes and/or relatively small-diameter cooling probes and/or close-together cooling probes and/or portable implementations are often simpler or exclusively implementable using such cooling probes. Any suitable material or combinations of material may be used in fashioning such cooling probes, for example stainless steel (e.g., surgical stainless steel), copper, and silver. That said, it is generally preferred to use a material that is a good thermal conductor to more effectively cool tissue. Materials having a good thermal conductivity (e.g., greater than about 50 W/mK, greater than about 100 W/mK and even greater than about 200 W/mK) include silver (429 W/mK), copper (400 W/mK), gold (310 W/mK), aluminum (237 W/mK) and aluminum alloys (~160 W/mK). Unfortunately, for some embodiments, materials having a good thermal conductivity are not sufficiently rigid and are therefore unsuitable for fashioning a cooling probe configured for piercing skin. In some embodiments, a cooling probe is fashioned of a material having only a fair thermal conductivity (e.g., between about 5 and about 50 W/mK) but having sufficient rigidity for piercing the skin such as stainless steel (16~W/mK). In some embodiments, a cooling probe is made of more than one material, at least one having a desirably high thermal conductivity and at least one having a desirable rigidity. For example, in some embodiments a cooling probe comprises a sharpened hollow tube of a rigid material (e.g, a 0.9 mm stainless steel hypodermic needle known in the art of insulin administration) with a solid material having a good thermal conductivity (e.g, silver or copper) filling the bore of the tube. For example, in some embodiments a cooling probe comprises a sharpened rod of a rigid material (e.g, a 0.5 mm stainless steel needle known in the art of acupuncture) coated with a layer of material having a good thermal conductivity (e.g, silver or copper).

In some embodiments, the individual cooling probes of the plurality of cooling probes are physically independent. In such embodiments, the cooling probes are generally contacted with the skin serially, so that using the device is relatively time consuming Further, even the most skilled of operators finds it somewhat challenging to contact each cooling probe at the correct location of the skin when the cooling probes are to be placed close together or at high density. To overcome some of these disadvantages, in some embodiments such cooling probes are used together with a template that is placed on the skin, the template showing where the cooling probes are to be placed. In some embodiments, the template is perforated and the cooling probes are passed through the perforations to contact the skin. In some embodiments, the template includes markings to indicate where the cooling probes should be placed, and the cooling probes are used to pierce the template. In some embodiments, the template has a side that is adhered to the skin of a subject (e.g., includes an adhesive): in such a way the template is in a fixed location where an operator wants to place the cooling probes. In some embodiments, the template is of a thermally insulating material (e.g., PTFE, PE, PP, nylon), protecting areas of skin not in contact with the cooling probes.

In some embodiments, the device further comprises a cooling-probe base, and cooling probes making up the plurality of cooling probes are secured to the cooling-probe base. In some embodiments, the cooling-probe base and the plurality of cooling probes consequently constitute a unitary cooling-probe assembly. In some such embodiments, the cooling probes are integrally formed with the cooling-probe base. In some such embodiments, the cooling probes are secured to the cooling-probe base substantially irremovably, e.g., are welded thereto. In some embodiments, the cooling probes are reversibly secured to the cooling-probe base, e.g., are screwed thereinto or removably pressed thereinto.

Generally, in such embodiments the proximal ends of the cooling probes contact a surface of the cooling-probe base and the distal ends of the cooling probes protrude outwards from the surface. In some such embodiments, the device further comprises a thermal insulator positioned between the cooling probes, usually in proximity to where the cooling probes contact the cooling probe, e.g, the thermal insulator is located around the proximal ends of the cooling probes. Such a thermal insulator reduces the extent of cooling (whether by physical contact or by radiative cooling) of skin by the cooling-probe base during the period of time when the cooling probes are maintained in contact with the area of skin. Any suitable material may be used as a thermal insulator. Suitable such materials include polypropylene (PP, 0.1-0.2 W/mK), polytetrafluoroethylene (PTFE, 0.25 W/mK), polyethylene (PE, 0.46 W/mK) and epoxy (0.35 W/mK). The thermal insulator is of any suitable form, e.g., a perforated sheet, strands, a layer.

Embodiments where the plurality of cooling probes are provided secured to a cooling-probe base have many advantages. As noted above, in some embodiments, there is importance to the number of probes per unit surface area contacting the skin, the size of the area of skin, the distance between distal tips of neighboring cooling probes, the shape of the area, and the arrangement of the cooling probes in the area. In embodiments where the plurality of cooling probes are provided secured to a cooling-probe base, contacting (whether surface contact or penetrating contact) of the plurality of cooling probes in the desired fashion may be performed, even by a less-skilled operator, simply, accurately and quickly, substantially requiring only one action to simultaneously bring all the distal ends in contact with the skin. For penetrating contact, such embodiments allow all distal tips of the cooling probes to be located at the desired depth. Apart from the ease of use, such treatment provides more uniform results with less chance of undesirable side effects such as partial skin discoloration due to inhomogeneous melanocyte death and causes less pain. Further, and in some embodiments no less importantly, such devices are typically significantly cheaper to manufacture, more portable and the cooling-probes are simpler to sterilize.

In some embodiments, a cooling-probe base is configured to transfer heat from the distal ends of the cooling probes secured thereto to a cooling region of the cooling-probe base, for example when the distal ends are in contact with skin. Such embodiments are exceptionally useful when (solid) cooling probes are configured to transfer heat from the distal end to a proximal end of the cooling probe by heat transfer through a solid material, especially when devoid of channels to accommodate the flow of cooling fluid.

In some such embodiments, the cooling-probe base is configured to transfer heat from the cooling probes to the cooling region of the cooling-probe base, in some such embodiments through solid material (e.g., the solid material from which the cooling-probe base is fashioned). In some such embodiments, the cooling-probe base and the cooling probes are devoid of channels for the flow of cooling fluid. In such embodiments, when the distal ends of the plurality of cooling probes are contacting an area of skin, the tissue is cooled by conducting heat from the distal ends of the cooling probes, through the contact with the cooling-probe base (usually through the proximal ends of the cooling probes), through the solid mass of the cooling-probe base to a cooling region of the cooling-probe base which is cooled, for example, by contact with a cool fluid or a cooling generator. Analogously to solid cooling probes, such cooling-probe bases are relatively easy to manufacture and use, relatively small and typically significantly cheaper. Further, such cooling-probe bases make implementation of portable devices practical. Any suitable material or combinations of material may be used in fashioning such cooling probes, for example stainless steel and copper.

Clearly, conductive heat transfer through a cooling-probe assembly comprising a plurality of solid small-dimensioned (and in some embodiments thin and elongated) cooling probes and a solid cooling-probe base without cooling fluid passing in the cooling probes or cooling-probe base is inefficient and slow. Yet, despite the fact that the body heat counters localized cooling, it has been found that it is possible to implement the methods described herein and achieve substantial cooling of a volume of tissue using such a cooling-probe assembly.

In some embodiments, the device is configured to allow application of a cooling material (e.g., a fluid or solid) to the cooling region of the cooling-probe base when the distal tips of the cooling probes are contacting skin of a subject, thereby allowing cooling of the distal ends of the cooling probes. Any suitable cooling material may be used in implementing such embodiments, for example liquid nitrogen, dry ice, a salt/ice solution. In some such embodiments, the device comprise a receptacle for holding a cooling fluid in contact with the cooling region of the cooling-probe base when the cooling probes are contacting skin of a subject, allowing cooling of the distal ends of the cooling probes.

In some embodiments, the device comprises an adaptor for functionally associating the cooling-probe base to a cooling generator when the cooling probes are contacting skin of a subject, so that a heat sink of the cooling generator is in thermal communication with the cooling region of the cooling-probe base allowing cooling of the distal ends of the cooling probes. In some embodiments, the adaptor is configured for reversibly functionally associating the cooling-probe base to a cooling generator. In some embodiments, the adaptor functionally associates the cooling-probe base to a cooling generator substantially irremovably. By cooling generator is meant any device or assembly that has a heat sink to "generate cooling", that is to say is suitable to remove heat from the distal ends of the cooling probes through the cooling region of the cooling-probe base into the heat sink of the cooling generator.

In some such embodiments, the cooling generator is a controllable cooling generator, that is to say is configured to controllably generate different degrees of cooling, allowing control of the temperature of the heat sink and consequently of the cooling probes. Controllable cooling generators reduce the risk of over-cooling and undesired freeze damage, as well as simple implementation of time-varying cooling regimes.

Any suitable cooling generator may be used in implementing such embodiments. Typical cooling generators include Peltier effect coolers, Joule-Thomson effect coolers, recuperative cryocoolers, regenerative cryocoolers, and Stirling cryocoolers. For example, suitable cooling generators are a K508 Integral Stirling 1/2W cryocooler by Ricor Cryogenic & Vacuum Systems Ltd. (Kibbutz Ein Harod Ihud, Israel), the cooling generator used in the Her Option(r) device (CooperSurgical, Inc., Trumbull Conn., USA), the Cryopen(r) (CryoPen Inc., Corpus Christi Tex., USA) or as described in U.S. Pat. Nos. 6,629,417; 6,017,337; 4,206,609.

In some embodiments, the device further comprises a cooling-generator functionally associated with the plurality of cooling probes, so that when the cooling-generator is activated the distal ends of the cooling probes are cooled. In some such embodiments, the device is portable. By portable is meant that the device (including a cooling generator if needed for operation of the device) is of dimensions that a single person can carry the device from one place to the other. In some embodiments, a portable device is entirely portable, including a power supply (e.g., includes integrated batteries). In some embodiments, a portable device requires a source of electrical power, for instance must be plugged into the power mains to be operable.

An embodiment of a dermatological treatment device as described herein, a portable dermatological treatment device 10 is schematically depicted in FIG. 1. In FIG. 1A, device 10 is depicted assembled and ready to use, including a cooling generator 12 and a cooling-probe assembly 14.

Cooling generator 12 is a modified K508 Integral Stirling 1/2W cryocooler by Ricor Cryogenic & Vacuum Systems Ltd. (commercially available from Kibbutz Ein Harod Ihud, Israel) and includes an integrated battery pack as a power supply. When activated, cooling generator 12 reduces the temperature of a heat sink 16 (a cold-finger) to a desired temperature as determined by the operator.

Cooling-probe assembly 14, substantially a solid block of copper metal machined to have a desired shape and features, is schematically depicted in FIG. 1B in perspective and in FIG. 1C in side cross section. A proximal end of cooling-probe assembly 14 constitutes a cooling-probe base 18 with a hollowed-out proximal side 20 to fit over heat sink 16 of cooling generator 12, thus functioning as an adaptor allowing reversible functional association of cooling-probe assembly 14 with cooling generator 12.

On a distal end 22 of cooling-probe assembly 14 are nine cooling probes 24 arranged in a 3×3 square matrix, machined from the original copper workpiece (e.g., using standard machine tools) and therefore integrally formed with cooling-probe assembly 14. All nine cooling probes 24 are identical in shape, having flattened distal tips 26 having a 1.5 mm×1.5 mm square cross section. Each cooling probe 24 is separated from a neighboring cooling probe 24 by 4 mm. Each cooling probe 24 is 5 mm long from distal end 22.

Encasing distal end 22 is thermal insulator 28, a sheath of 4 mm thick high density polyethylene, including nine square perforations allowing passage of cooling probes 24 therethrough. As a result, thermal insulator 28 is positioned between cooling probes 24 while distal ends 30 of cooling probes 24 protrude 1 mm therefrom.

For use (for example for reducing the color of a superficial birthmark or for rejuvenating an area of skin), an operator activates cooling generator 12. The inner faces of the walls defining the hollowed-out portions of proximal side 20 function as the cooling region of cooling-probe base 18. Heat sink 16 of cooling generator 12 cools cooling-probe base 18 and consequently distal ends 30 and distal tips 26 of cooling probes 24, in accordance with the teachings herein.

The operator brings distal tips 26 to make non-penetrating contact with an area of skin for a desired period of time. Since the area defined by the edges of cooling probes 24 is 90 mm2 (9.5×9 5 mm) and the total contacted area is 20 mm2 (9 cooling probes 24, each with a 1.5×1.5 mm distal tip 26), only 22% of the area of skin is contacted by cooling probes 24. When the period of time has passed, the operator moves distal tips 26 of cooling probes 24 of device 10 away from the area of skin.

Device 10 includes an integrated battery pack as a power supply and is therefore entirely portable. In some embodiments, a portable device such as 10 does not include an integrated power supply and must be connected to the power mains to be operated.

In device 10, cooling-probe assembly 14 is configured to be reversibly functionally associated with cooling generator 12. In some embodiments, a cooling-probe assembly 14 of a device such as 10 is irreversibly functionally associated with a cooling generator 12, for example a cooling-probe base 18 is part of a heat sink 16, or is substantially permanently secure thereto, for example by welding.

An additional embodiment of a dermatological treatment device, device 32, is schematically depicted in FIGS. 2. In FIG. 2A, device 32 is depicted assembled and ready to use, including a cooling generator 12 (a Cryopen(r), CryoPen Inc., Corpus Christi Tex., USA) and a cooling-probe assembly 14.

Figure 2B:
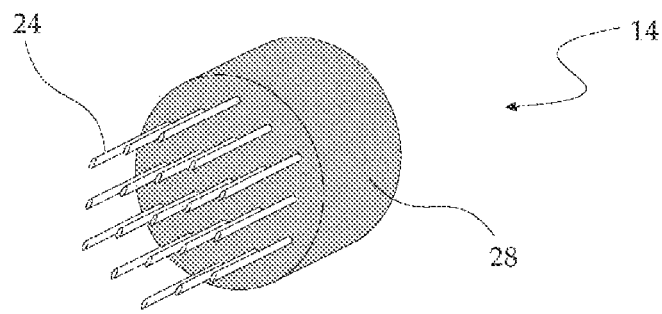
Figure 2C:
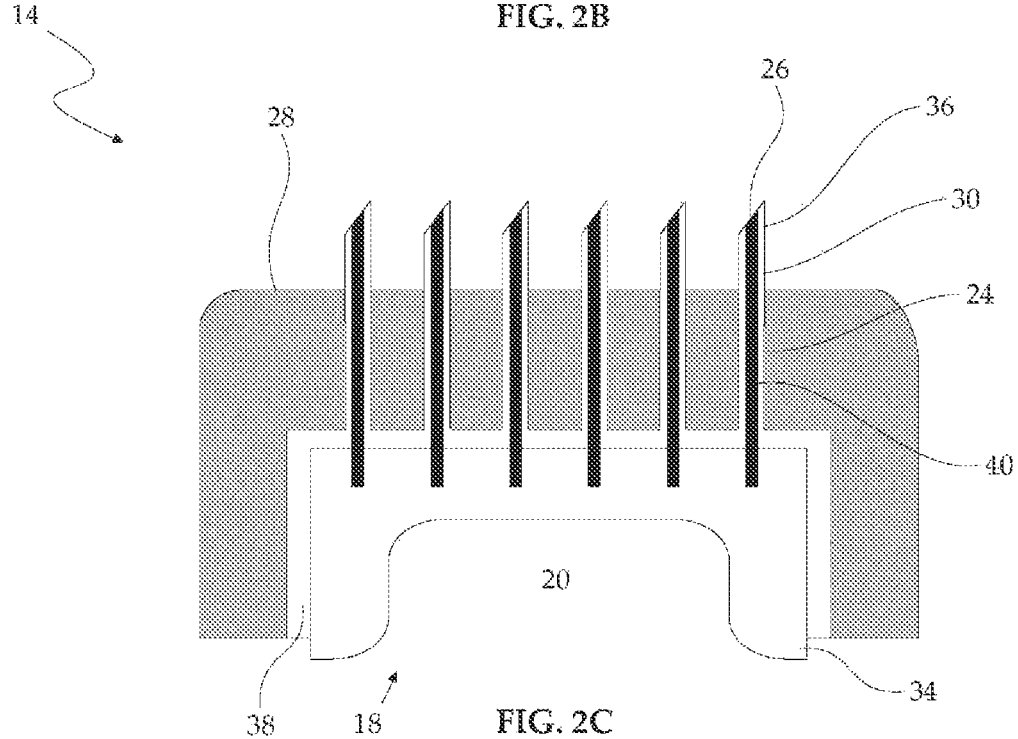

Like device 10, device 32 comprises a unitary cooling-probe assembly 14 including a cooling-probe base 18 and a plurality of cooling probes 24, schematically depicted in perspective in FIG. 2B and in side cross-section in FIG. 2C.

Cooling-probe assembly 14 comprises nineteen cooling probes 24 arranged in a hexagonal array five cooling-probes wide, each cooling probe 24 separated by 2 mm from a neighboring cooling probe 24.

Cooling-probe base 18 comprises a solid block of copper 34 with having a proximal side 20 configured to act as an adaptor allowing cooling-probe assembly 14 to be reversibly functionally associated with cooling generator 12 and also functioning as a cooling region of cooling-probe base 18.

In device 32, cooling probes 24 are irremovably secured to cooling-probe base 18. Specifically, each cooling probe 24 comprises a 6 mm long 0.9 mm outer diameter stainless steel hollow sharpened needle 36 welded to a 0.5 mm thick stainless steel base 38 secured to copper block 34 so that the bores of needles 36 are colinear with holes drilled in copper block 34. Copper powder is placed in the bores and melted therein so that cooling probes 24 comprise a solid copper core 40 in contact with copper block 34 passing through the bore of stainless steel needles 36.

Like device 10, cooling-probe assembly 14 of device 32 comprises a thermal insulator 28 located between cooling probes 24, a sheath of 4 mm-thick high density polyethylene, including perforations allowing passage of cooling probes 24 therethrough. As a result, thermal insulator 28 is positioned between cooling probes 24 while distal ends 30 of cooling probes 24 protrude 2 mm therefrom. As discussed hereinbelow, thermal insulator 28 also functions as a penetration stop, physically preventing cooling probes 24 from penetrating more than 2 mm into the skin.

For use (for example for the treatment of pigmentation blemishes), an operator coats distal ends 30 of cooling probes with a lubricant (e.g., glycerin) and pushes distal tips 26 into an area of skin so that distal tips 26 pierce the skin, allowing distal ends 30 of cooling probes to make penetrating contact with the area of skin. Thermal insulator 28 acts as a physical penetration stop so that distal tips 26 are brought to a depth of 2 mm.

The operator activates cooling generator 12. The inner faces of the walls defining the hollowed-out portions of proximal side 20 function as the cooling region of cooling-probe base 18. Cooling generator 12 cools copper block 34 of cooling-probe base 18 which cools stainless steel base 38 and stainless steel needles 36. Due to the high thermal conductivity of copper, copper cores 40 transfer heat more efficiently than stainless steel needles 36, so distal ends 30 of cooling probes 24 are cooled more efficiently and homogeneously than if cooling probes 24 were devoid of copper cores 40.

When the desired period of time has passed, the operator withdraws cooling probes 24 from the area of skin.

In some embodiments, cooling generator 12 is activated prior to cooling probes 24 making contact with area of skin. In some embodiments, such cooling has a numbing effect and even less discomfort is felt than without such cooling.

Figure 3:
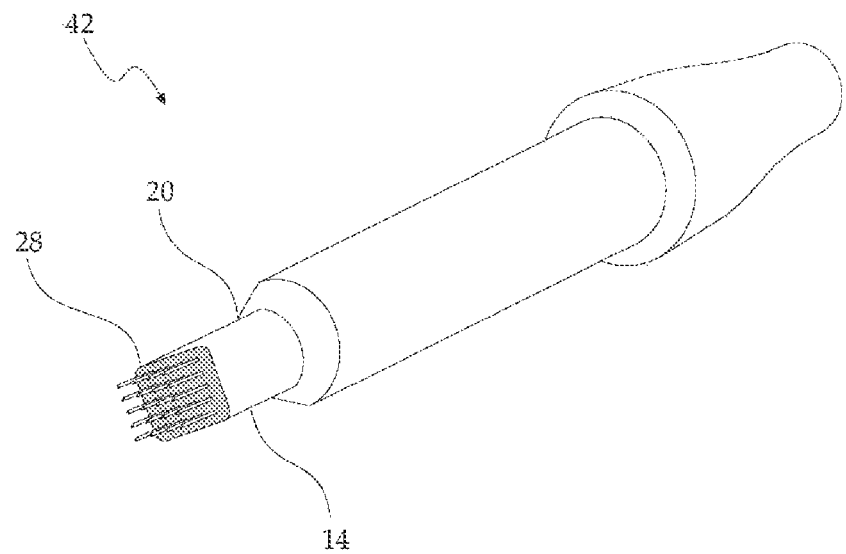
FIG. 3 is a schematic depictions of an additional embodiment of a device as described herein including a plurality of cooling probes arranged in a rectangular array configured for piercing skin and making penetrating contact with skin.

A cooling-probe assembly 14 of an additional embodiment of a dermatological treatment device 42 is schematically depicted in FIG. 3. Device 42 is substantially the same as device 32, excepting cooling-probe assembly 14.

Cooling-probe assembly 14 depicted in FIG. 3 comprises twenty cooling probes 24 arranged in a 4×5 rectangular array, each cooling probe 24 separated by 1.5 mm from a neighboring cooling probe 24.

Like in device 32, a copper block of a cooling-probe base of device 42 has a proximal side 20 configured to act as an adaptor allowing cooling-probe assembly 14 to be reversibly functionally associated with a cooling generator.

In device 42, cooling probes 24 are 10 mm long 0.5 mm diameter sharpened stainless steel needles (similar to acupuncture needles). Each cooling probe 24 is embedded 2 mm into the copper block of the cooling-probe base and protrudes 5 mm from holes in a 3 mm thick thermal insulator 28, allowing penetrating contact with an area of skin to a depth of 5 mm.

The use of device 42 is substantially the same as the use of device 32.

Figure 4:
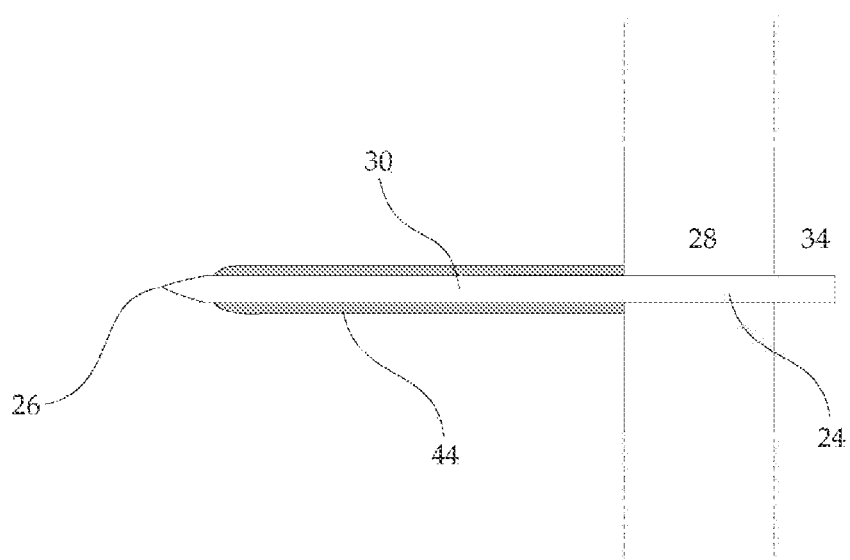
FIG. 4 is a schematic depiction of an embodiment of a single cooling probe configured for piercing skin and making penetrating contact with skin.

In FIG. 4, a single cooling probe 24 of an embodiment of a device related to device 42, is schematically depicted in cross section. Cooling probe 24 depicted in FIG. 4 is configured to allow substantial cooling of tissue only near or at distal tip 26. Cooling probe 24 depicted in FIG. 4 is substantially identical to cooling probes 24 of device 42, except that most of distal end 30, excluding distal tip 26, is covered with a layer 44 of a thermally insulating material (e.g., polyethylene, PTFE). When used, for example in accordance with the teachings herein, penetration of cooling probes 24 depicted in FIG. 4 cause physical damage but contact as described herein does not lead to substantial cooling of tissue. Rather, only a volume of tissue in proximity to distal tip 26 is substantially cooled in accordance with the teachings herein. Use of such a cooling probe 24 as described herein, allows for minor damage near the surface of skin, but more extensive cold damage deeper in the skin, for example, providing limited damage to the epidermis with more extensive damage to the dermis. Such embodiments are also exceptionally useful for treating deep pigmentation blemishes.

Figure 5:
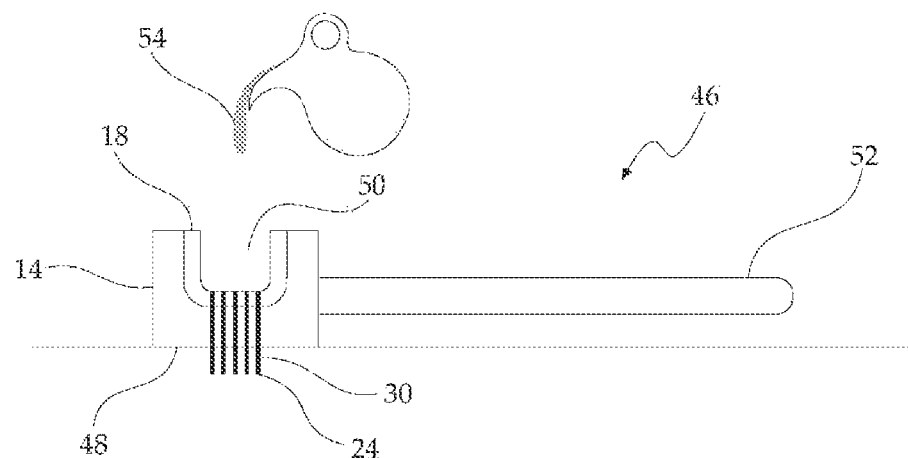
FIG. 5 is a schematic depictions of an additional embodiment of a device as described herein including cooling probes configured for piercing skin and making penetrating contact with skin.

A device 46, including a cooling-probe assembly 14 similar to that of device 32 but configured to be operated without a cooling generator is schematically depicted in FIG. 5 contacting an area of skin 48 in side cross section. Cooling-probe assembly 14 of device 46 is not configured to be functionally associated with a cooling generator. Instead, a side of cooling-probe base 18 of cooling-probe assembly 14 opposite cooling probes 24 is hollowed so as to constitute a receptacle 50. Device 46 further includes a handle 52 of PTFE.

For use, as seen in FIG. 5, cooling-probes 24 are penetratingly contacted with area of skin 48 as described above so that receptacle 50 is facing substantially upwards. While cooling-probe assembly 14 is held steady using handle 52, a cooling material 54 (e.g., liquid nitrogen, salt/ice solution, dry ice) is placed in receptacle 50. The inner faces of the walls defining container 50 function as the cooling region of cooling-probe base 18. Cooling material 54 in receptacle 50 cools cooling-probe base 18 and consequently distal ends 30 of cooling probes 24, in accordance with the teachings herein. Contact with area of skin 48 is maintained for a period of time in accordance with the decision of the operator. If desired, additional cooling material 54 may be added to receptacle 50. When the period of time has passed, the operator moves device 46 away from the area of skin with the help of handle 52.

Figure 6:
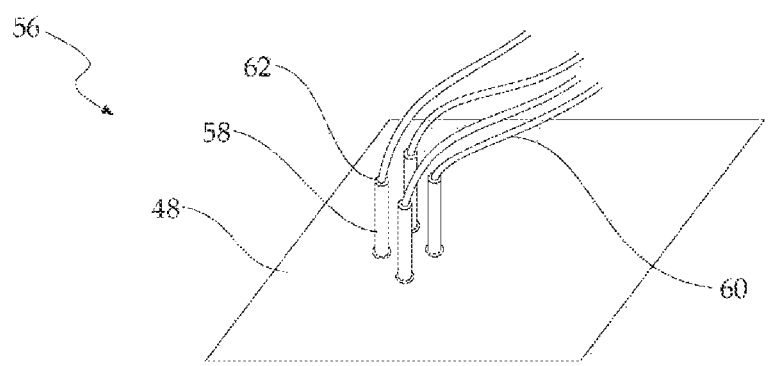
FIG. 6 is a schematic depictions of an additional embodiment of a device as described herein including four independent cooling probes configured for piercing skin and making penetrating contact with skin.

A portion of an additional device, device 56 is schematically depicted in FIG. 6. In FIG. 6, distal tips and distal ends of the four physically-independent cooling probes 58 of device 56 are depicted while making penetrating contact with an area of skin 48 of a subject.

Each one of cooling probes 58 is configured for piercing human skin and for making penetrating contact in accordance with the teachings herein. Each cooling probe 58 is 1.7 mm wide and is similar in construction to the taught in U.S. Pat. No. 6,503,246, comprising cooling fluid channels to accommodate the flow of a cooling fluid such as liquid nitrogen.

Not depicted in FIG. 6 is the necessary bulky cooling generator that generates the required cooling fluid and the control system, pumps, valves, fittings and tubing required to direct the cooling fluid into the channels in cooling probes.

For use, cooling probes 58 are inserted serially, one after the other, for example in accordance with the methods described herein. A cooling fluid supply tube 60 is secured to a distal end 62 of each cooling probe 58, providing fluid communication between the cooling fluid channels of cooling probes 58 and the cooling generator.

The cooling generator is activated and the generated cooling fluid is directed through the channels, cooling the distal ends of cooling probes 58.

Figure 7:
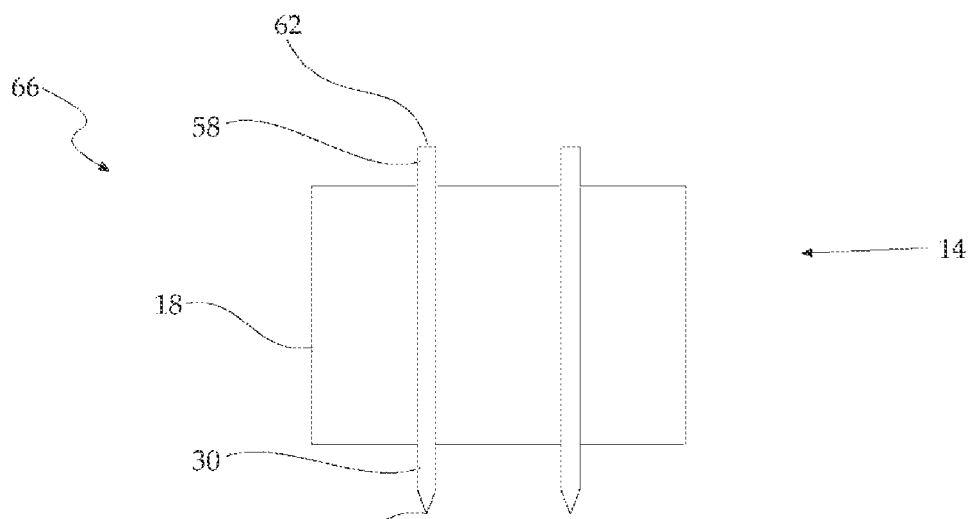
FIG. 7 is a schematic depictions of an additional embodiment of a device as described herein including four cooling probes configured for piercing skin and making penetrating contact with skin.

An embodiment related to device 56, device 66 is depicted in FIG. 7. Device 66 is similar to device 56 but also comprises a cooling-probe base 18, substantially a PTFE block with four holes drilled therethrough, each hole configured to reversibly accommodate a cooling probe 58. When cooling probes 58 are pushed into and held in the holes of cooling-probe base 18, the assembly constitutes a unitary cooling-probe assembly 14 that, as described above, has a number of advantages including allowing simultaneous contact of distal tips 26 of all four cooling probes 58 with skin as well as accurate spacing and arrangement of distal tips 26 during contact with skin. Further, cooling-probe base 18 functions as a penetration stop, ensuring that distal tips 26 all penetrate to a desired depth into the skin.

It is important to note that an additional advantage of methods for treating skin as described herein, whether by adversely effecting melanocytes, adipocytes or other embodiments is the discussed with relation to skin rejuvenation. In some embodiments, the localized damage caused by the cooling so that there is a plurality of damaged loci surrounded by healthy tissue leads to a skin rejuvenation effect in analogy to "fractional technology" methods known in the art. Additionally, in some embodiments where the cooling probes make penetrating contact with the area of skin, there is an additional "fractional technology" effect caused by the mechanical damage caused by the penetration of the skin by the plurality of cooling probes. As a result, in some embodiments, in addition to the primary desired effect for which a treatment is applied there is an added advantage of quick and esthetic healing.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

The invention claimed is:

1. A dermatological treatment device comprising: a plurality of cooling probes secured to a cooling-probe base, each said cooling probe having a distal end with a distal tip configured for non-penetrating surface contact with skin of a subject, where each said cooling probe is configured to allow cooling of a respective said distal end; said cooling probes configured so that when said plurality of cooling probes contacts skin of a subject, the distance between distal tips of two neighboring said cooling probes is not more than about 10 mm, wherein said distal tip of said cooling probe has a cross-sectional area of not more than about 3.14 mm$^2$, said cooling probe extends not less than 10 mm from said cooling-probe base to said distal tip;

and said distal end of said cooling probe is configured to transfer heat from said distal end to the cooling-probe base only by conduction through a solid material.

2. The device of claim 1, wherein said plurality of cooling probes comprises at least four said cooling probes.

3. The device of claim 1, wherein said cooling probes are configured so that when said plurality of cooling probes contacts skin of a subject, there are at least 4 cooling probes per cm$^2$ of skin.

4. The device claim 1, wherein said cooling probes are configured to be arranged in an array when contacting the skin of a subject.

5. The device of claim 1 wherein a said cooling probe is configured to allow substantial cooling only of said distal tip of said distal end of said cooling probe.

6. The device of claim 1, wherein said cooling probe is devoid of channels to accommodate the flow of cooling fluid.

7. The device of claim 1, further comprising a thermal insulator positioned between said cooling probes.

8. The device of claim 1, further comprising an adaptor for functionally associating said cooling-probe base to a cooling generator when said cooling probes are contacting skin of a subject, so that a heat sink of said cooling generator is in thermal communication with said cooling region of said cooling-probe base allowing cooling of said distal ends of said cooling probes.

9. The device of claim 8, wherein said adaptor is configured for reversibly functionally associating said cooling-probe base to a cooling generator.

10. The device of claim 1, further comprising a cooling-generator functionally associated with said plurality of cooling probes.

11. The device of claim 10, wherein the device is portable.

12. The device of claim 1, wherein said distal tip of said cooling probe has a cross-sectional area of between about 0.79 mm$^2$ and about 3.14 mm$^2$.

13. A method of dermatological treatment of an area of skin of a subject, comprising:
   a) on an area of skin of a subject, contacting a plurality of non-penetrating cooling probes secured to a cooling-probe base, each cooling probe having a distal end with a distal tip; and
   b) maintaining said plurality of cooling probes in said contact with the area of skin for a period of time while said distal ends of said plurality of cooling probes are at a probe temperature of not more than about 5° C. so as to substantially cool a volume of tissue by transfer of heat from said distal end to the cooling-probe base only by conduction through a solid material;

wherein during said maintaining said contact, the distance between distal tips of two neighboring said cooling probes is not more than about 10 mm, said cooling probe extends not less than 10 mm from said cooling-probe base to said distal tip; and said distal tip of said cooling probe has a cross-sectional area of between about 0.79 mm$^2$ and about 3.14 mm$^2$, thereby causing a beneficial effect as a result of said substantial cooling of said volume of tissue at a comparatively moderate rate.

14. The method of claim 13, wherein the treatment is a medical treatment.

15. The method of claim 13, wherein the treatment is a non-medical cosmetic treatment.

16. The method of claim 13, wherein the beneficial effect is at least partially caused by cold damage to portions of said substantially cooled volume of tissue.

17. The method of claim 13, wherein the treatment is for skin rejuvenation and said beneficial effect is an improved appearance of said area of skin.

18. The method of claim 13, wherein the beneficial effect is at least partially caused by cold damage to at least some melanocytes in said substantially cooled volume of tissue.

19. The method of claim 18, wherein the treatment is for skin lightening and said beneficial effect is lightening the color of said area of skin.

20. The method of claim 18, wherein the treatment is for treating a pigmentation blemish of the skin and said beneficial effect is reducing the severity of said pigmentation blemish.

21. The method of claim 13, wherein the beneficial effect is at least partially caused by cold damage to at least some adipocytes in said substantially cooled volume of tissue.

22. The method of claim 21, wherein the treatment is for reducing the effect of undesired adipocytes and said beneficial effect is reducing the volume of fat under said area of skin.

23. The method of claim 13, wherein said plurality of cooling probes comprises at least four said cooling probes.

24. The method of claim 13, wherein during said maintaining contact, the area of skin is in contact with at least about 4 cooling probes per cm$^2$.

* * * * *